(12) United States Patent
Mizuno et al.

(10) Patent No.: US 8,962,245 B2
(45) Date of Patent: Feb. 24, 2015

(54) METHOD FOR PRODUCING CIRCULAR DNA FORMED FROM SINGLE-MOLECULE DNA

(75) Inventors: Shinichi Mizuno, Kurume (JP); Koji Nagafuji, Kurume (JP); Takashi Okamura, Kurume (JP)

(73) Assignee: Kurume University, Fukuoka (JP)

( * ) Notice: Subject to any disclaimer, the term of this patent is extended or adjusted under 35 U.S.C. 154(b) by 0 days.

(21) Appl. No.: 13/819,396

(22) PCT Filed: Aug. 22, 2011

(86) PCT No.: PCT/JP2011/068856
§ 371 (c)(1),
(2), (4) Date: Feb. 27, 2013

(87) PCT Pub. No.: WO2012/029577
PCT Pub. Date: Mar. 8, 2012

(65) Prior Publication Data
US 2013/0164757 A1 Jun. 27, 2013

(30) Foreign Application Priority Data

Sep. 2, 2010 (JP) ................................. 2010-196719

(51) Int. Cl.
*C12Q 1/68* (2006.01)
*C12P 19/34* (2006.01)
*C07H 21/04* (2006.01)
*C12N 15/10* (2006.01)
*C12N 15/64* (2006.01)

(52) U.S. Cl.
CPC ................ *C07H 21/04* (2013.01); *C12N 15/10* (2013.01); *C12N 15/1096* (2013.01); *C12N 15/64* (2013.01); *C12Q 1/6806* (2013.01); *C12Q 2525/307* (2013.01)
USPC .......................................... 435/6.1; 435/91.1

(58) Field of Classification Search
None
See application file for complete search history.

(56) References Cited

U.S. PATENT DOCUMENTS

| 8,352,194 | B1 | 1/2013 | Blanck |
| 2006/0292611 | A1 | 12/2006 | Berka et al. |
| 2008/0090776 | A1 | 4/2008 | Mano et al. |
| 2009/0176652 | A1 | 7/2009 | Dahl et al. |
| 2012/0202214 | A1 | 8/2012 | Omi |
| 2013/0102006 | A1 | 4/2013 | Takeuchi et al. |

FOREIGN PATENT DOCUMENTS

| JP | 2008-504805 | 2/2008 |
| JP | 2008-295444 | 12/2008 |
| JP | 2008-545448 | 12/2008 |
| JP | 2011-510669 | 4/2011 |
| WO | 2006/003721 | 1/2006 |
| WO | 2009/032167 | 3/2009 |
| WO | 2009/098037 | 8/2009 |
| WO | 2011/043220 | 4/2011 |
| WO | 2011/162295 | 12/2011 |
| WO | 2012/014795 | 2/2012 |
| WO | 2013/006195 | 1/2013 |
| WO | 2013/018882 | 2/2013 |

OTHER PUBLICATIONS

Supplementary European Search Report issued Jan. 22, 2014 in European Application No. 11 82 1594.
Fullwood et al., "Next-generation DNA sequencing of paired-end tags (PET) for transcriptome and genome analyses", Genome Research, vol. 19, 2009, pp. 521-532.
Soda et al., "Identification of the transforming EML4-ALK fusion gene in non-small-cell lung cancer", Nature, vol. 448, Aug. 2, 2007, pp. 561-567.
Tomlins et al., "Recurrent Fusion of TMPRSS2 and ETS Transcription Factor Genes in Prostate Cancer", Science, vol. 310, Oct. 28, 2005, pp. 644-648.
Illumina, "Preparing 2-5kb Samples for Mate Pair Library Sequencing", Part # 1005363, Rev. B, Feb. 2009.
Bashir et al., "Evaluation of Paired-End Sequencing Strategies for Detection of Genome Rearrangements in Cancer", PLoS Computational Biology, vol. 4, Issue 4, Apr. 2008.
Metzker, M., "Sequencing technologies—the next generation", Nature Reviews, vol. 11, Jan. 2010, pp. 31-46.
Mitelman et al., "Fusion genes and rearranged genes as a linear function of chromosome aberrations in cancer", Nature Genetics, vol. 36, No. 4, Apr. 2004, pp. 331-334.
Ruan et al., "Multiplex parallel pair-end-ditag sequencing approached in system biology", Wires Systems Biology and Medicine, vol. 2, Mar./Apr. 2010, pp. 224-234.
International Preliminary Report on Patentability and Written Opinion of the International Searching Authority issued Mar. 14, 2013 in International Application (PCT) No. PCT/JP2011/068856.
International Search Report issued Nov. 22, 2011 in International Application (PCT) No. PCT/JP2011/068856.
International Search Report issued Nov. 13, 2012 in corresponding International Application No. PCT/JP2012/071492.
International Preliminary Report on Patentability issued Mar. 4, 2014 in corresponding International Application No. PCT/JP2012/071492.

*Primary Examiner* — Kenneth R. Horlick
*Assistant Examiner* — David Thomas
(74) *Attorney, Agent, or Firm* — Wenderoth, Lind & Ponack, L.L.P.

(57) ABSTRACT

There is provided a method for producing a circular DNA which consists of a circular DNA formed from a single-molecule DNA and which does not comprise circular DNA formed from multiple-molecule DNA. According to the method of the present invention, a circular DNA molecule formed only from a single-molecule DNA can be reliably produced.

11 Claims, 6 Drawing Sheets

SEQUENCE LISTING

```
<160> NUMBER OF SEQ ID NOS: 4

<210> SEQ ID NO 1
<211> LENGTH: 17
<212> TYPE: DNA
<213> ORGANISM: Artificial
<220> FEATURE:
<223> OTHER INFORMATION: one strand of adaptor (b)
<220> FEATURE:
<221> NAME/KEY: misc_feature
<222> LOCATION: (7)..(11)
<223> OTHER INFORMATION: n is a, c, g, or t

<400> SEQUENCE: 1
gcagtgnnnn ncactgc                                                   17

<210> SEQ ID NO 2
<211> LENGTH: 12
<212> TYPE: DNA
<213> ORGANISM: Artificial
<220> FEATURE:
<223> OTHER INFORMATION: adaptor (A)

<400> SEQUENCE: 2
ccagaattct gg                                                        12

<210> SEQ ID NO 3
<211> LENGTH: 39
<212> TYPE: DNA
<213> ORGANISM: Artificial
<220> FEATURE:
<223> OTHER INFORMATION: SMART IV oligonucleotide

<400> SEQUENCE: 3
aagcagtggt atcaacgcag agtggccatt acggccggg                           39
```

```
<210> SEQ ID NO 4
<211> LENGTH: 58
<212> TYPE: DNA
<213> ORGANISM: Artificial
<220> FEATURE:
<223> OTHER INFORMATION: CDS III/3' PCR primer
<220> FEATURE:
<221> NAME/KEY: misc_feature
<222> LOCATION: (58)..(58)
<223> OTHER INFORMATION: n is a, c, g, or t

<400> SEQUENCE: 4
attctagagg ccgaggcggc cgacatgttt tttttttttt tttttttttt tttttttn       58
```

METHOD FOR PRODUCING CIRCULAR DNA FORMED FROM SINGLE-MOLECULE DNA

TECHNICAL FIELD

The present invention relates to a method for producing circular DNA that is formed only from single-molecule DNA, a novel adapter used in the above-mentioned method, and a kit for producing circular DNA, comprising the novel adapter.

The present invention further relates to a method for identifying and/or detecting a gene using single-molecule circular DNA produced by the above-mentioned method. In particular, the invention relates to a method for identifying and/or detecting a fusion gene that causes various pathologic conditions.

BACKGROUND ART

Vector method is a conventional gene analysis method. In the vector method, a target gene to be analyzed is incorporated into a vector, and the full-length sequence of the gene obtained after the proliferation is then determined using a sequencer. However, the vector method is problematic in that it needs a culture operation, and also in that a sequencer should be used to analyze the full length of a gene.

In recent years, a high speed sequencer used in gene analysis has been developed, and with the development of this sequencer, mate-pair method as a gene analysis means has attracted attention.

FIG. 1 schematically shows the outline of gene analysis using the mate-pair method. In the mate-pair method, a nucleotide sequence for ligation (a restriction enzyme recognition site) is attached to the both ends of the target gene to be analyzed, and the target gene is then circularized. Then, a part including 15 nucleotides or more, and preferably 25 nucleotides or more to several tens of nucleotides or less, of both sides flanking to the restriction enzyme recognition site is cleaved from the circularized gene, generally using a type II restriction enzyme. The part is amplified by PCR, and the nucleotide sequence of the cleaved partial gene is then determined. Thereby, the sequences of both ends of the target gene are determined, and the target gene can be then identified using known sequence data. Mate pair means the sequence data of a pair of nucleotide sequences obtained by reading both ends of a single DNA fragment.

Practically used methods of cleaving a given number of nucleotides from a gene include: a method of cutting sites apart from the recognition site using a type II restriction enzyme to cleave a given number of nucleotides out; and a method comprising physically cutting circular DNA using Sonication or the like, recovering a cleaved fragment with biotin attached to the linker, then amplifying the fragment by PCR, and then determining the sequence of the amplified PCR product.

The mate-pair method can, therefore, identify a known gene by reading a certain length of nucleotide sequence including the both sides flanking to the ligation site in a gene circularized by ligating the both ends of the DNA. Basically, if partial nucleotide sequences of the head and tail portions of a gene were read, these sequences would allow a reliable discrimination among individual genes. Accordingly, the mate-pair method has been adopted as a reliable and simple gene analysis method (Non Patent Literatures 1 and 2). Moreover, the mate-pair method has been applied to the next generation sequence analysis, and thus it has become increasingly important together with the emergence of a high speed sequencer.

However, when a DNA is circularized for gene analysis according to the mate-pair method, besides the self-circularization of a single gene or a single DNA (a single molecule), the circularization of a plurality of DNAs (a plurality of molecules) and the linear binding of a plurality of molecules (two or more molecules) also take place. A linear molecule consisting of a plurality of molecules can be separated and eliminated from a circular molecule by the subsequent operations. On the other hand, a circular molecule consisting of a plurality of molecules cannot be separated from a circular molecule consisting of a single molecule, and it becomes a contaminant. A circular product consisting of a plurality of molecules inhibits individual gene analyses and significantly decreases analytical specificity for the following reasons. Specifically, as shown in FIG. 2, when three types of cDNAs are to be self-circularized, if only single-molecule DNA is circularized as shown in (B), a gene can be specified using precise sequences according to the mate-pair method. However, other than the circularization of a single molecule as shown in (B), an uncircularized linear product may be generated as shown in (C), or two or more cDNAs may be circularized as shown in (D). In the case of (C), the linear product can be eliminated with DNA exonuclease. However, in the case of (D), a circularized product consisting of a plurality of cDNAs is recognized as a circularized molecule, and thus, it cannot be eliminated and becomes a contaminant in the gene analysis according to the mate-pair method.

The gene analysis according to the mate-pair method intends to identify a target gene based on the nucleotide sequences of both ends of the target gene. Specifically, a ligation adapter for circularization is attached to both ends of individual genes, and the two adapter sites are then ligated to each other to circularize the gene. Then, a part including a certain number of nucleotides at both sides with the adapter site being the center is cleaved from the gene. Consequently, the gene can be identified by analyzing the nucleotide sequence of a portion from each end of the original gene. Hence, a circularized product of a plurality of molecules has a plurality of adapter sites, and the two ends attached to an adapter are ends of different genes. Accordingly, as described above, since gene analysis is carried out by cleaving a part including nucleotide sequences of a given number of nucleotides of the both ends attached to the adapter, with the adapter being the center, according to either one of the above described two methods, the gene fragment for the analysis obtained from circularized products of a plurality of molecules comprises ends of different genes. Thus, the analysis of a single gene cannot be carried out.

As such, in the gene analysis according to the mate-pair method, the presence of a circularized product of a plurality of molecules inhibits each gene analysis.

The probability of circularization of a plurality of DNA molecules generally ranges from few to dozen percent, depending on the method applied. In the analysis of a known gene, they are recognized as abnormal nucleotide sequences and thus, elimination of them from the sequence to be analyzed is usually possible. Hence, it causes only a slight decrease in accuracy, although the operation becomes complicated. However, in a case in which the mate-pair method is used to detect the presence of an abnormal gene, such as a fusion gene, in a group of normal genes, if a plurality of normal genes are circularized, it is determined that abnormal genes are present. As a result, it becomes impossible to accurately confirm the presence of an abnormal gene such as a fusion gene.

The fusion gene is a gene with a novel function that is constructed by binding a plurality of (two) genes to each other. For example, abnormalities in chromosome structure, such as deletion, overlapping, recombination and translocation, are found in a cancer cell. When the cleavage and ligation of a gene occur at a DNA level and a structural gene is present at each cleavage point, a fusion gene is formed.

In general, a fusion gene is lethal or senseless to cells, and it does not cause clinical problems in many cases. However, when cell growth is abnormally promoted as a result that a fusion protein generated from such a fusion gene inhibits the control of the cell growth, it causes clinical problems such as tumor formation.

It had been considered that the fusion gene is mainly expressed in hematopoietic tumors. In recent years, however, it has been expected that the fusion gene would be also associated with epithelial solid tumors (Non Patent Literature 3). Among such solid cancers, responsible fusion genes have been discovered from prostatic cancer and lung cancer (Non Patent Literatures 4 and 5).

From these findings, the analysis of a fusion gene, namely, confirmation of the presence of a fusion gene, has attracted attention as a novel method for diagnosing tumors (cancers) and the like. Specifically, by detecting a known fusion gene that has been known as corresponding to pathologic conditions, it becomes possible to make a rapid diagnosis of the pathologic conditions. Furthermore, the discovery of a novel fusion gene leads to the discovery of drug discovery targets.

On the other hand, conventional chromosome analyses performed on solid tumors had had a certain limit, and it had been extremely difficult to analyze and/or confirm a fusion gene. Recently, novel methods, such as the cDNA functional expression analysis method according to Mano et al., have been developed. However, these techniques have been still insufficient in terms of complicated operations, problems regarding accuracy, etc. (Patent Literature 1). In addition, various types of next-generation high speed gene sequencers have been recently developed. Thus, high speed sequence analysis of genes has significantly progressed, and gene analysis in a short time has been realizing. Hence, searching for fusion genes have been started according to high-speed and/or high-scale nucleotide sequence analysis of tumor genomes and/or genes (Non Patent Literature 6).

In order to identify a fusion gene by sequence analysis using the mate-pair method, it is essential to reliably produce single circular DNA from a single cDNA molecule. A schematic view of the analysis of a fusion gene according to the mate-pair method is shown in FIG. 3. There is a case, however, in which single circular DNA may be formed from a plurality of cDNA molecules, as shown in FIG. 4. Thus, when sequence analysis is carried out according to the mate-pair method, the result that a normal gene appears as a fusion gene may be obtained. If this gene is eliminated for the reason that it is not present in a conventional gene sequence, a fusion gene is also eliminated. As a result, it becomes substantially impossible to confirm the presence of a fusion gene.

When a fusion gene is to be detected by the sequence analysis according to the mate-pair method, it is essential to eliminate circularized cDNA of a plurality of genes.

LIST OF CITATION

Patent Literature

Patent Literature 1: Japanese Patent No. 4303303

Non Patent Literature

Non Patent Literature 1: *Tanpakushitsu Kakusan Koso*, August 2009, (1233-1247, 1271-1275)
Non Patent Literature 2: "*Shikkan Idenshi no Tansaku to Chokosoku Sequence,*" *Jikken Iqaku* extra edition, Vol. 27, No. 12 (2009, 113 (1929)-143 (1959))
Non Patent Literature 3: Mitelman et al., 2004, Nature Genetics, Vol. 36, No. 4, pp. 331-334
Non Patent Literature 4: Chinnaiyan et al., 2005, Science, Vol. 310, pp. 644-648
Non Patent Literature 5: Soda et al., 2007, Nature, Vol. 448, pp. 561-566
Non Patent Literature 6: Bashir et al., April 2008, PLoS Computational Biology, Vol. 4, Issue 4, e1000051

SUMMARY OF INVENTION

Technical Problem

It is desired to discover a method for reliably producing a circular DNA molecule formed only from a single-molecule DNA. That is to say, it is an object of the present invention to provide a method capable of producing a single circularized DNA from a single DNA.

Solution to Problem

The present inventors have found that a circularized DNA consisting only of a single molecule can be formed by introducing an adapter having a specific structure comprising a specific sequence recognition site into a single DNA molecule and then performing two-step ligation. The inventors have found a method for reliably circularizing only single-molecule DNA, wherein circularization of multiple molecules consisting of a plurality of DNAs does not take place.

In a first embodiment, the present invention provides a method for producing a circular DNA which consists of a circular DNA formed from single-molecule DNA and which does not comprise circular DNA formed from a multiple-molecule DNA, the method comprising the following steps:
1) a step of binding an adapter (A) for a first circularization to one end of each DNA molecule of interest, and binding to the other end thereof an adapter (B) for a second circularization comprising an adapter (b) and the adapter (A), wherein the adapter (B) binds to the DNA molecule via the adapter (b) side, such that the adapter (A) in the adapter (B) is located outside the bond of the DNA molecule to the adapter (b), wherein
the adapter (A) comprises a cleavage site generating a cleavage end non-specifically binding to all of the cleavage ends of the adapter (A), and
the adapter (b) comprises a cleavage site generating a cleavage end specifically binding only to a cleavage end from the same adapter (b);
2) a first cleavage step of cleaving the DNA molecule obtained in step 1) at the cleavage site of the adapter (A);
3) a first circularization step of binding both ends of the DNA molecule obtained in step 2) to circularize the DNA molecule;
4) a step of eliminating an uncircularized linear single-molecule and a multiple-molecule-bound DNA in step 3);

5) a second cleavage step of cleaving the circular DNA molecule obtained in step 3) and step 4) at the cleavage site of the adapter (b); and 6) a second circularization step of binding both ends of the DNA molecule obtained in step 5) to circularize the DNA molecule.

In the second circularization step, since the adapter (b) specifically binds to a cleavage end from the same adapter (b), linearization caused by circularization of a plurality of DNA molecules substantially does not take place, and the DNA to be circularized is a single-molecule DNA. At this time, the uncircularized linear DNA molecules need to be eliminated, as described above.

The linear DNAs that are not circularized in step 6) consist of: a trace amount of single-molecule DNA, which have failed to rebind the portion (b) cleaved in step 5); and a major amount of single-molecule or multiple-molecule DNAs, which have be circularized with a plurality of DNA molecules in step 3) and have failed to rebind each adapter (b) after the cleavage of the adapter in step 5).

In the first embodiment of the present invention, the adapter (A) is preferably double-stranded DNA comprising a restriction enzyme site recognizing a sequence whose cleavage ends are complementary to each other, and it is, for example, double-stranded DNA comprising a restriction enzyme site recognizing a palindromic sequence.

In addition, in a second embodiment, the present invention provides a method for producing a single circular DNA which consists of a circular DNA formed from a single-molecule DNA and which does not comprise a circular DNA formed from a multiple-molecule DNA, the method comprising the following steps:

1) a step of binding an adapter (A) for a first circularization to one end of each DNA molecule of interest, and binding to the other end thereof an adapter (B) for a second circularization comprising an adapter (b) and the adapter (A), wherein the adapter (B) binds to the DNA molecule via the adapter (b) side, such that the adapter (A) in the adapter (B) is located outside the bond of the DNA molecule to the adapter (b), wherein the adapter (A) is a double-stranded DNA comprising a restriction enzyme site recognizing a palindromic sequence, and the adapter (B) comprises the adapter (b) and the adapter (A), wherein the adapter (b) is a double-stranded DNA comprising identical nick-generating enzyme recognition sites or restriction enzyme sites being reversely oriented to each other, wherein the adapter (b) is a double-stranded DNA comprising a double-stranded DNA sequence having a unique sequence for each adapter (b) between the identical nick-generating enzyme recognition sites or restriction enzyme sites being reversely oriented to each other, and if the adapter (b) is cleaved at the identical nick-generating enzyme recognition sites or restriction enzyme sites being reversely oriented to each other, the cleavage site rebinds only to the cleavage site from the same adapter (b);

2) a first cleavage step of cleaving the DNA molecule obtained in step 1) with a restriction enzyme recognizing the restriction enzyme site comprised in the adapter (A);

3) a first circularization step of ligating both ends of the DNA molecule obtained in step 2) to circularize the DNA molecule;

4) a step of eliminating an uncircularized linear single-molecule and a multiple-molecule-bound DNA in step 3);

5) a second cleavage step of cleaving the circular DNA molecule obtained in step 3) and step 4) with a nick-generating enzyme or a restriction enzyme recognizing the nick-generating enzyme recognition sites or restriction enzyme sites of the adapter (b); and 6) a second circularization step of ligating both ends of the DNA molecule obtained in step 5) to circularize the DNA molecule.

Preferably, the above described second embodiment of the present invention further comprises a step of digesting with endonuclease a circularized DNA formed by binding the adapters (b) via cleavage sequence sites being partially different from each other (miss annealing) and circularization in the above described step 6). Thereby, circular DNA consisting of a plurality of molecules can be more reliably eliminated.

In the second embodiment of the present invention, preferably, the adapter (A) is a double-stranded DNA comprising a restriction enzyme site X recognizing a palindromic sequence, and the adapter (B) is a double-stranded DNA consisting of two DNA strands complementary to each other having the following structure $y_1$-Y-$y_2$-X:

[Formula 1]

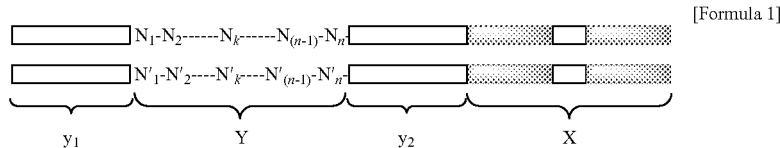

wherein

X represents a double-stranded DNA being a restriction enzyme site recognizing a palindromic sequence;

$y_1$ and $y_2$ represent double-stranded DNAs respectively comprising identical nick-generating enzyme recognition sites or restriction enzyme sites being reversely oriented to each other;

Y represents a double-stranded DNA sequence having a unique sequence for each DNA molecule to be circularized, n represents an integer of 1 to 40, $N_1$ to $N_n$, which may be the same or different, each represent a deoxyribonucleotide selected from the group consisting of dAMP, dCMP, dGMP and dTMP, and $N'_1$ to $N'_n$ represent the following deoxyribonucleotides respectively corresponding to the $N_1$ to $N_n$,

TABLE 1

| $N_k$ | $N'_k$ |
|---|---|
| dAMP | dTMP |
| dCMP | dGMP |
| dGMP | dCMP |
| dTMP | dAMP | wherein k represents an integer from 1 to n.

In the above structure, n is 1 to 40, preferably 4 to 15, and more preferably 5 to 10. However, even if n is more than 40, the method of the present invention can be carried out.

In this embodiment, preferably, $y_1$ and $y_2$ respectively comprise the nick-generating enzyme recognition sites, and more preferably, the nick-generating enzyme is Nb.BtsI that recognizes 6 nucleotides, or Nt.BsqQI that recognizes 7 nucleotides. Alternatively, $y_1$ and $y_2$ may respectively comprise the restriction enzyme sites.

In a third embodiment, the present invention provides an adapter for producing a circular DNA, consisting of two DNA strands complementary to each other having the following structure $y_1$-Y-$y_2$-X:

[Formula 2]

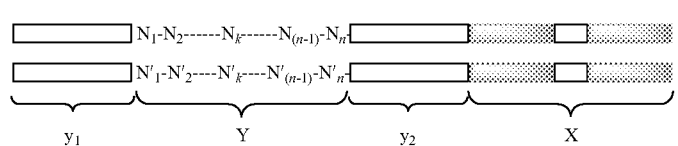

wherein
X represents a double-stranded DNA that is a restriction enzyme site recognizing a palindromic sequence;
$y_1$ and $y_2$ represent double-stranded DNAs respectively comprising identical nick-generating enzyme recognition sites or restriction enzyme sites being reversely oriented to each other;
Y represents a double-stranded DNA sequence having a unique sequence for each DNA molecule to be circularized, n represents an integer of 1 to 40, $N_1$ to $N_n$, which may be the same or different, each represent a deoxyribonucleotide selected from the group consisting of dAMP, dCMP, dGMP and dTMP, and $N'_1$ to $N'_n$ represent the following deoxyribonucleotides respectively corresponding to the $N_1$ to $N_n$,

TABLE 2

| $N_k$ | $N'_k$ |
|---|---|
| dAMP | dTMP |
| dCMP | dGMP |
| dGMP | dCMP |
| dTMP | dAMP | wherein k represents an integer from 1 to n.

In the above structure, n is 1 to 40, preferably 4 to 15, and more preferably 5 to 10. However, even if n is more than 40, the method of the present invention can be carried out.

The above described adapter in the third embodiment of the present invention corresponds to the adapter (B) in the second embodiment of the present invention, and it is preferably used in the method of the present invention for producing a circular DNA which consists of a circular DNA formed from a single-molecule DNA and which does not comprise a circular DNA formed from a multiple-molecule DNA.

In the third embodiment of the present invention, preferably, $y_1$ and $y_2$ respectively comprise nick-generating enzyme recognition sites, and more preferably, the nick-generating enzyme is Nb.BtsI that recognizes 6 nucleotides, or Nt.BsqQI that recognizes 7 nucleotides. Alternatively, $y_1$ and $y_2$ may respectively comprise restriction enzyme sites.

In a fourth embodiment, the present invention further provides a kit for producing a circular DNA comprising the adapter according to the above described third embodiment (which is also simply referred to as adapter (B)) and an adapter consisting of a double-stranded DNA comprising a restriction enzyme site identical to the restriction enzyme site represented by X comprised in the adapter (B) (which is also simply referred to as adapter (A)).

In a fifth embodiment, the present invention also provides a method for producing a cDNA library, comprising using the method according to the above described first or second embodiment.

In a sixth embodiment, the present invention further provides a method for identifying a gene by subjecting a circular DNA molecule obtained by using the method according to the above described first or second embodiment to a mate-pair method, the method comprising the following steps:

1) a step of reading nucleotide sequences, each consisting of 15 to 600 nucleotides, flanking to both sides of an adapter (B) in a circular DNA molecule obtained by using the method according to the above described first or second embodiment; and 2) a step of identifying a gene contained in the circular DNA molecule by comparing the read nucleotide sequences with the sequences of both ends of a known gene.

The nucleotide sequence to be read consists of preferably 15 to 100 nucleotides, and more preferably 25 to 35 nucleotides. However, the method of the present invention can also be carried out by reading a nucleotide sequence consisting of 600 or more nucleotides.

In a seventh embodiment, the present invention further provides a method for detecting a fusion gene by subjecting a circular DNA molecule obtained by using the method according to the above described first or second embodiment to a mate-pair method, the method comprising the following steps:

1) a step of reading nucleotide sequences, each consisting of 15 to 600 nucleotides, flanking to both sides of an adapter (B) in a circular DNA molecule obtained by using the method according to the above described first or second embodiment; and 2) a step of comparing the read nucleotide sequences with the sequences of both ends of a known gene, wherein if the genes of both ends correspond to known different genes, the gene comprised in the circular DNA molecule is identified to be a fusion gene.

The nucleotide sequence to be read consists of preferably 15 to 100 nucleotides, and more preferably 25 to 35 nucleotides. However, the method of the present invention can also be carried out by reading a nucleotide sequence consisting of 600 or more nucleotides.

In the seventh embodiment of the present invention, when the sequences of both sides flanking to both sides of the adapter (B) correspond to the ends of both sides of a known fusion gene, the known fusion gene is detected. When the relationship between the known fusion gene and a disease has been known, there is provided a method for detecting a disease characterized by the expression of the fusion gene detected by the method of the seventh embodiment, wherein the fusion gene is used as a marker.

On the other hand, when the sequences flanking to both sides of the adapter (B) correspond to the terminal sequences of different genes and do not correspond to the ends of both sides of a known fusion gene, the gene contained in the circular DNA molecule is identified to be a novel fusion gene. In this case, the detected novel fusion gene is preferably used in drug discovery screening.

Advantageous Effects of Invention

Using the adapter and method of the present invention, the accuracy of gene analysis is significantly improved. In addition, unconventional high-accuracy mate-pair analysis becomes possible, and thus, the adapter and method of the present invention are provided as tools extremely useful for genomic analysis. In particular, by applying the method of the present invention to the production of a cDNA library, it is highly likely to discover a novel fusion gene. That is to say, by reliably achieving circularization of a single DNA molecule, it becomes possible to develop novel diagnostic tool and/or method.

According to the present invention, a method for circularizing only a single-molecule DNA, wherein circularization of a plurality of molecules is substantially prevented with regard to circularization of DNA, is provided, so that problems regarding contamination in gene analysis such as mate-pair analysis can be solved, and so that high-accuracy analysis becomes possible. Moreover, by applying the method of the present invention to detection and/or analysis of a fusion gene, high-accuracy analysis of a fusion gene becomes possible, and a useful diagnostic tool can be provided.

BRIEF DESCRIPTION OF DRAWINGS

FIG. 8 is a schematic view showing application of the method of the present invention to a genomic library.

DESCRIPTION OF EMBODIMENTS

Figure 1:
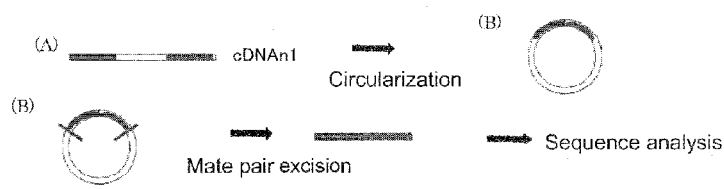
FIG. 1 schematically shows an outline of the gene analysis according to the mate-pair method.
Figure 2:
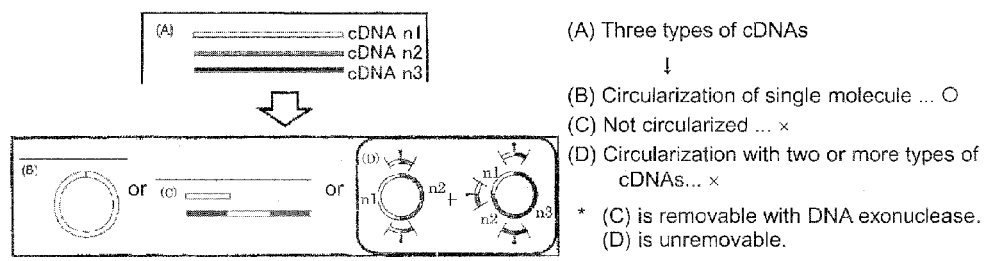
FIG. 2 schematically shows problems with the gene analysis according to the mate-pair method.
Figure 3:
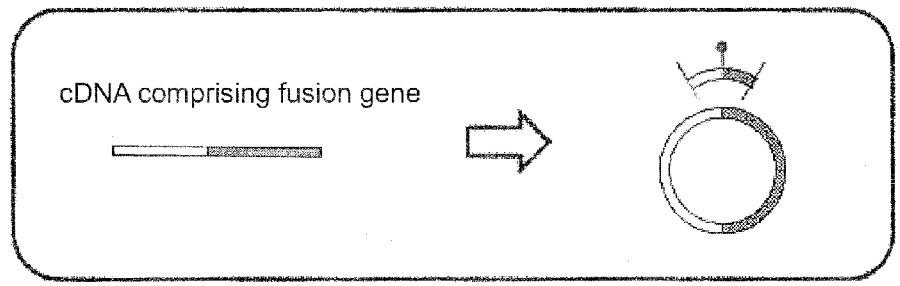
FIG. 3 is a schematic view showing the analysis of a fusion gene according to the mate-pair method.
Figure 4:
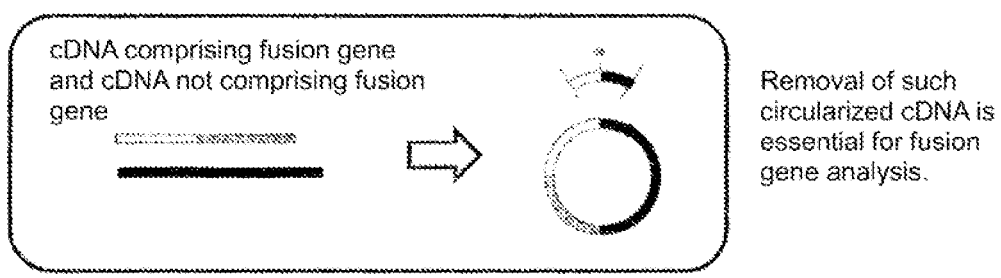
FIG. 4 schematically shows problems with the analysis of a fusion gene according to the mate-pair method.

Regarding a First Embodiment of the Present Invention

In a first embodiment, the present invention provides a method for producing a circular DNA which consists of a circular DNA formed from a single-molecule DNA and which does not comprise a circular DNA formed from a multiple-molecule DNA, the method comprising the following steps:

1) a step of binding an adapter (A) for a first circularization to one end of each DNA molecule of interest, and binding to the other end thereof an adapter (B) used for a second circularization comprising an adapter (b) and the adapter (A), wherein the adapter (B) hinds to the DNA molecule via the adapter (b) side, such that the adapter (A) in the adapter (B) is located outside the bond of the DNA molecule to the adapter (b), wherein the adapter (A) comprises a cleavage site generating a cleavage end non-specifically binding to all of the cleavage ends of the adapter (A), and the adapter (b) comprises a cleavage site generating a cleavage end specifically binding only to a cleavage end from the same adapter (b);

2) a first cleavage step of cleaving the DNA molecule obtained in step 1) at the cleavage site of the adapter (A);

3) a first circularization step of binding both ends of the DNA molecule obtained in step 2) to circularization the DNA molecule;

4) a step of eliminating an uncircularized linear single-molecule and a multiple-molecule-bound DNA in step 3);

5) a second cleavage step of cleaving the circular DNA molecule obtained in step 3) and step 4) at the cleavage site of the adapter (b); and 6) a second circularization step of binding both ends of the DNA molecule obtained in step 5) to circularization the DNA molecule.

The above described first embodiment of the present invention relates to a technique of circularizing substantially only a single gene (DNA), such that circularization of a plurality of genes (DNAs) can be prevented.

Specifically, the method of the first embodiment of the present invention is characterized in that it comprises two-step circularization.

Hereinafter, the method of the first embodiment will be described in the order of steps.

Step 1) is a step of binding an adapter (A) for a first circularization to one end of each DNA molecule of interest, and binding to the other end thereof an adapter (B) used for a second circularization comprising an adapter (b) and the adapter (A). Herein, the adapter (B) binds to the DNA molecule via the adapter (b) side, such that the adapter (A) in the adapter (B) is located outside the bond of the DNA molecule to the adapter (b). Specifically, the adapter (A) is allowed to bind to one end of each DNA molecule of interest, and the adapter (B) is allowed to bind to the other end, so that the adapter (A) in the adapter (B) is located on the side closer to the end than the adapter (b) is. As a result, the adapters (A) are located on both ends of each DNA molecule of interest.

It is to be noted that the adapter (A) comprises a cleavage site generating a cleavage end non-specifically binding to all of the cleavage ends of the adapter (A), and that the adapter (b) comprises a cleavage site generating a cleavage end specifically binding only to a cleavage end from the same adapter (b). That is to say, the adapter (A) does not exhibit binding specificity and enables non-specific binding between all cleavage ends from the adapter (A). In contrast, the adapter (b) has a constitution that is different depending on each DNA molecule of interest, and it is able to rebind to only cleavage ends from the same adapter (b) and is not able to rebind to cleavage ends from a different adapter (b).

Step 2) is a first cleavage step of cleaving the DNA molecule obtained in step 1) at the cleavage site of the adapter (A).

Since the adapters (A) bind to both ends of the DNA molecule obtained in step 1), cleavage ends from the adapters (A) are generated on both ends of each DNA molecule as a result of the first cleavage step.

Step 3) is a first circularization step of binding both ends of the DNA molecule obtained in step 2) to circularize the DNA molecule. The first circularization is circularization with the adapters (A), and such circularization occurs as a result that cleavage ends from the adapters (A) generated on both ends of each DNA molecule bind to each other. Herein, the adapter (B), as well as the adapters (A), is incorporated into the circular molecule during the first circularization. As described above, the function of the adapter (A) does not have specificity, and does not have selectivity by the rebinding of both ends of the DNA molecule of interest. Thus, not only the binding of both ends of a single DNA molecule at the adapter (A) portions, but circularization by the binding of both ends of each of a plurality of DNA molecules, also takes place. That is, because of the function of the adapter (A), circularization of a plurality of molecules, as well as single-molecule circularization, takes place. A circularized product from such a plurality of molecules naturally comprises a plurality of the adapters (B).

Step 4) is a step of eliminating an uncircularized linear single-molecule and a multiple-molecule-bound DNA in step 3).

Step 5) is a second cleavage step of cleaving the circular DNA molecule obtained in step 3) and step 4) at the cleavage site of the adapter (b). That is to say, cleavage is carried out at the adapter (b) incorporated into each DNA molecule that has been circularized in step 3), such that a linear molecule is generated. By the second cleavage step, cleavage ends from the adapters (b) are generated on both ends of each DNA molecule. In this step, the cleavage end generated as a result of the cleavage substantially cannot bind to a cleavage end from another circular molecule.

Step 6) is a second circularization step of binding both ends of the DNA molecule obtained in step 5) to circularize the DNA molecule. That is to say, the cleavage ends from the adapters (b) are present on both ends of each DNA molecule obtained in step 5). As described above, the adapter (b) has a constitution that is different depending on each DNA molecule of interest, and it is able to rebind to only cleavage ends from the same adapter (b) and is not able to rebind to cleavage ends from a different adapter (b). Thus, as a result of the binding of cleavage ends from the adapters (b) on both ends of the same DNA molecule, second circularization takes place. Because of the specificity of the adapter (b), only single-molecule DNA of interest is circularized. That is, the adapter (b) has binding specificity, and when each adapter (b) portion is cleaved, it rebinds only to a portion, to which it has bound in the original circularized product, but it cannot rebind to other portions, upon rebinding circularization. Accordingly, when rebinding and circularization are carried out in the case of circularization of a plurality of molecules, only the rebinding and circularization in a plurality of the original molecules are possible. As described later, this probability is extremely low, and it is substantially 0 (zero). The probability of circularization of a single molecule is generally high because of its concentration, and as a result, only circularization of a single molecule takes place substantially. Uncircularized linear molecules can be separated and eliminated by allowing exonuclease to act on them.

As far as the adapters (A) and (b) perform the above-mentioned functions, the structures thereof are not particularly limited. When these adapters are double-stranded DNAs, an example of the adapter (A) is an adapter comprising a restriction enzyme site recognizing a palindromic structure, whereas an example of the adapter (b) is double-stranded DNA consisting of nucleic acids of at least 4 nucleotides, and preferably 5 or more nucleotides, which are complementary to each other, wherein the double-stranded DNA generates single-stranded ends complementary to each other, as a result of cleavage. However, the adapters (A) and (b) are not limited thereto. For instance, another example of the adapter (b) may be a substance that becomes a key and a keyhole as a result of cleavage. In a word, when the adapter (b) is cleaved and is then rebound, it may be an adapter that can rebind substantially only to the adapter before the cleavage. However, even in the case of a cleavage site having a non-palindromic sequence, the method of the present invention can be applied. In such a case, a configuration, in which an upstream adapter (A1) is distinguished from a downstream adapter (A2) and in which (A1) binds to (A2), is adopted. In this case, it is anticipated that the efficiency of single-molecule circular DNA at the first step will be slightly increased, in comparison with the use of an ordinary adapter (A).

According to the first embodiment of the present invention, circularized products from a plurality of genes (a plurality of molecules), which become contaminants, can be eliminated from, for example, gene analysis and gene identification according to the mate-pair method, and it becomes possible to produce circularized products only from a single molecule (a single gene).

Regarding a Second Embodiment of the Present Invention

The a second embodiment of the present invention provides a method for producing a circular DNA which consists of a circular DNA formed from a single-molecule DNA and which does not comprise a circular DNA formed from a multiple-molecule DNA, the method comprising the following steps:

1) a step of binding an adapter (A) for a first circularization to one end of each DNA molecule of interest, and binding to the other end thereof an adapter (B) for a second circularization comprising an adapter (b) and the adapter (A), wherein the adapter (B) binds to the DNA molecule via the adapter (b) side, such that the adapter (A) in the adapter (B) is located outside the bond of the DNA molecule to the adapter (b), wherein the adapter (A) is a double-stranded DNA comprising a restriction enzyme site recognizing a palindromic sequence, and the adapter (B) comprises the adapter (b) and the adapter (A), wherein the adapter (b) is a double-stranded DNA comprising identical nick-generating enzyme recognition sites or restriction enzyme sites being reversely oriented to each other, wherein the adapter (b) is a double-stranded DNA comprising a double-stranded DNA sequence having a unique sequence for each adapter (b) between the identical nick-generating enzyme recognition sites or restriction enzyme sites being reversely oriented to each other, and if the adapter (b) is cleaved at the identical nick-generating enzyme recognition sites or restriction enzyme sites being reversely oriented to each other, the cleavage site rebinds only to the cleavage site from the same adapter (b);

2) a first cleavage step of cleaving the DNA molecule obtained in step 1) with a restriction enzyme recognizing the restriction enzyme site comprised in the adapter (A);

3) a first circularization step of ligating both ends of the DNA molecule obtained in step 2) to circularize the DNA molecule;

4) a step of eliminating an uncircularized linear single-molecule and a multiple-molecule-bound DNA in step 3);
5) a second cleavage step of cleaving the circular DNA molecule obtained in step 3) and step 4) with a nick-generating enzyme or a restriction enzyme recognizing the nick-generating enzyme recognition sites or restriction enzyme sites of the adapter (b); and
6) a second circularization step of ligating both ends of the DNA molecule obtained in step 5) to circularize the DNA molecule.

In the second embodiment of the present invention, it is preferable that the production method further comprise a step of digesting with endonuclease a circularized DNA formed by binding the adapters (b) via cleavage sequence sites being partially different from each other and circularization in the above described step 6).

Hereafter, the second embodiment of the present invention will be described along the steps thereof, while referring to FIGS. 5 and 6.

Figure 5:
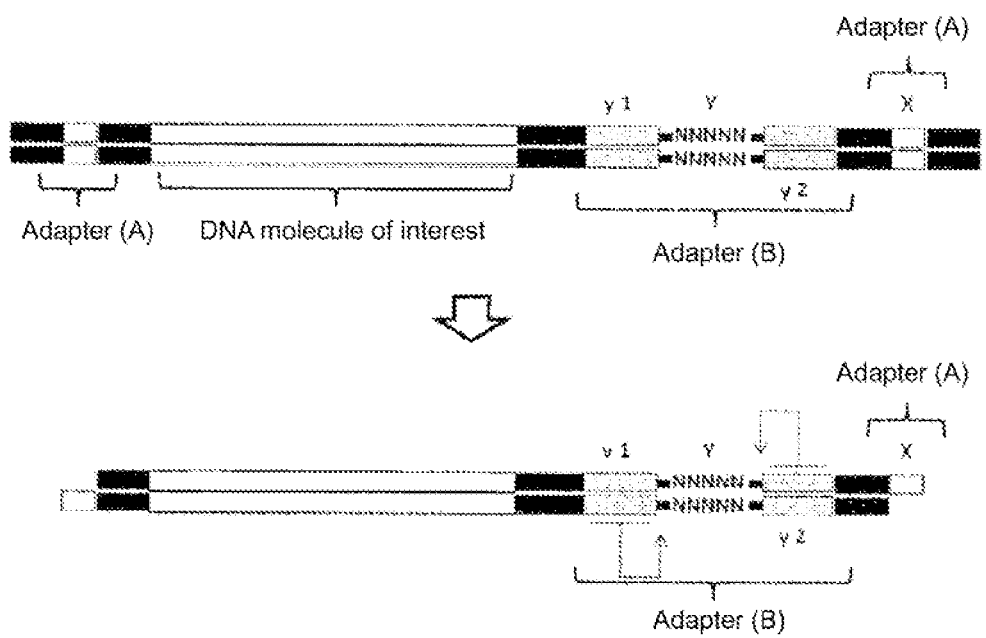
FIG. 5 schematically shows a first cleavage step in the two-step circularization method according to the present invention.

As schematically shown in FIG. 5, step 1) is a step of binding an adapter (A) for a first circularization to one end of each DNA molecule of interest, and binding to the other end thereof an adapter (B) used for a second circularization comprising an adapter (b) and the adapter (A). Herein, the adapter (B) binds to the DNA molecule via the adapter (b) side, such that the adapter (A) in the adapter (B) is located outside the bond of the DNA molecule to the adapter (b).

Herein, the adapter (A) is a double-stranded DNA comprising a restriction enzyme site recognizing a palindromic sequence; and the adapter (B) comprises the adapter (b) and the adapter (A), wherein the adapter (b) is a double-stranded DNA comprising identical nick-generating enzyme recognition sites or restriction enzyme sites being reversely oriented to each other, wherein the adapter (b) is a double-stranded DNA comprising a double-stranded DNA sequence having a unique sequence for each adapter (b) between the identical nick-generating enzyme recognition sites or restriction enzyme sites being reversely oriented to each other, and if the adapter (b) is cleaved at the identical nick-generating enzyme recognition sites or restriction enzyme sites being reversely oriented to each other, the cleavage site rebinds only to the cleavage site from the same adapter (b).

The adapters (A) and (b) will be described in detail below.

Adapter (A): This adapter is a sequence for cleaving the DNA molecule with restriction enzymes in the first cleavage and then performing gene ligation to produce circular DNA. Accordingly, the adapter (A) may comprise any type of restriction enzyme site, as long as the restriction enzyme site recognizes a palindromic sequence. Preferably, the adapter (A) comprises a restriction enzyme site recognizing a rare gene sequence that hardly cleaves the DNA of interest. Examples of the restriction enzyme site comprised in the adapter (A) include NotI and EcoRI.

```
                                            [Formula 3]
    EcoRI       NotI
     ∇           ∇
    GAATTC      GCGGCCGC
    CTTAAG      CGCCGGCG
     Δ           Δ
```

Adapter (b): This adapter is a double-stranded DNA comprising identical nick-generating enzyme recognition sites or restriction enzyme sites being reversely oriented to each other, wherein it comprises a double-stranded DNA sequence having a unique sequence for each adapter (b) between the identical nick-generating enzyme recognition sites or restriction enzyme sites being reversely oriented to each other. This nick-generating enzyme recognition site or restriction enzyme site is used to cleave the DNA molecule in the second cleavage so as to form a gene overhang specific to each molecule. The nick-generating enzyme cleaves only one DNA strand by nick cleavage, whereas the restriction enzyme cleaves two DNA strands simultaneously. Both of these recognition sites can be introduced. When the adapter (b) is cleaved at the identical nick-generating enzyme recognition sites or restriction enzyme sites being reversely oriented to each other, cleavage sites are generated. The cleavage sites rebind only to cleavage sites from the same adapter (b). In the case of using the nick-generating enzyme, the length of the cleavage site is not limited. In the case of using the restriction enzyme, however, the length of the cleavage site is limited, as shown in the following examples. Thus, in order to arbitrarily adjust the length of the cleavage site, the nick-generating enzyme is preferable.

Specific examples of each of the nick-generating enzyme recognition site and the restriction enzyme site will be given below.

In Case of Nick-Generating Enzyme Recognition Site

```
                                            [Formula 4]
Nb.BtsI (nick-generating enzyme)
GCAGTGNN
CGTCACNN
   Δ
When two Nb.BtsI sequences are reversely
oriented as shown below, the number N of
nucleotides is basically not limited.
       ∇
GCAGTGNNNNNNCACTGC
CGTCACNNNNNNGTGACG
   Δ
```

Restriction Enzyme Case 1

```
                                            [Formula 5]
BbsI (restriction enzyme)
       ∇
GAAGACNNNNNN
CTTCTGNNNNNN
           Δ
In this case, the number N is limited to 4
nucleotides.
```

Restriction Enzyme Case 2

[Formula 6]

```
BstXI (restriction enzyme)
         ∇
CCANNNNNNTGG
GGTNNNNNNACC
         Δ
```
In this case, the number N is limited to 4 nucleotides.

Restriction Enzyme Case 3

[Formula 7]

```
BaeI (restriction enzyme)
        ∇                        ∇
NNNNN(N10)AC(N4)GTAYC(N7)NNNNN
NNNNN(N10)TG(N4)CATRG(N7)NNNNN
Δ                        Δ
```
In this case, the number N is limited to 5 nucleotides.

In the case of this form, it is necessary to prepare two sites of N sequences that are equivalent to each other, by applying a method of extending primers from a loop structure, etc.

Subsequently, a cleavage site, which is generated when the adapter (b) is cleaved at the identical nick-generating enzyme recognition sites or restriction enzyme sites being reversely oriented to each other, will be described.

The cleavage site is a portion corresponding to a gene overhang specific to each molecule. As described above, when the cleavage site is produced with the restriction enzyme, the number of nucleotides is limited. On the other hand, when the cleavage site is produced with the nick-generating enzyme, the length of the cleavage site can be arbitrarily set. In order to achieve high specificity, a greater number of nucleotides constituting such a cleavage site is appropriate. In contrast, if the cleavage site is too long, it is highly likely that gene ligation will occur due to mismatch. When complexity is increased, such as the case of genome, it is desirable that the number of nucleotides constituting the cleavage site should be set to be greater, and at the same time, a step of digestion with endonuclease should be added to prevent the possibility of mismatch ligation (miss annealing). It is to be noted that a random combination is applied to the sequence of a cleavage site, and each different cleavage site is designed for each DNA molecule.

A specific example will be given below, while the number of nucleotides is set at "5". As an example, an adapter (B) having the following sequence is produced by nucleic acid synthesis, and then, it can be used in the method of the present invention.

[Formula 8]

```
         Adaptor (B) (example)
      Nb.BtsI                NotI
         ∇                     ∇
 -GCAGTGNNNNNCACTGC--GCGGCCGC-
 -CGTCACNNNNNGTGACG--CGCCGGCG-
         Δ                     Δ
      Nb.BtsI
   y1 ___Y___        y2 ___X___
```

Step 2) is a first cleavage step of cleaving the DNA molecule obtained in step 1) with a restriction enzyme recognizing the restriction enzyme site comprised in the adapter (A) (FIG. 5).

Figure 6:
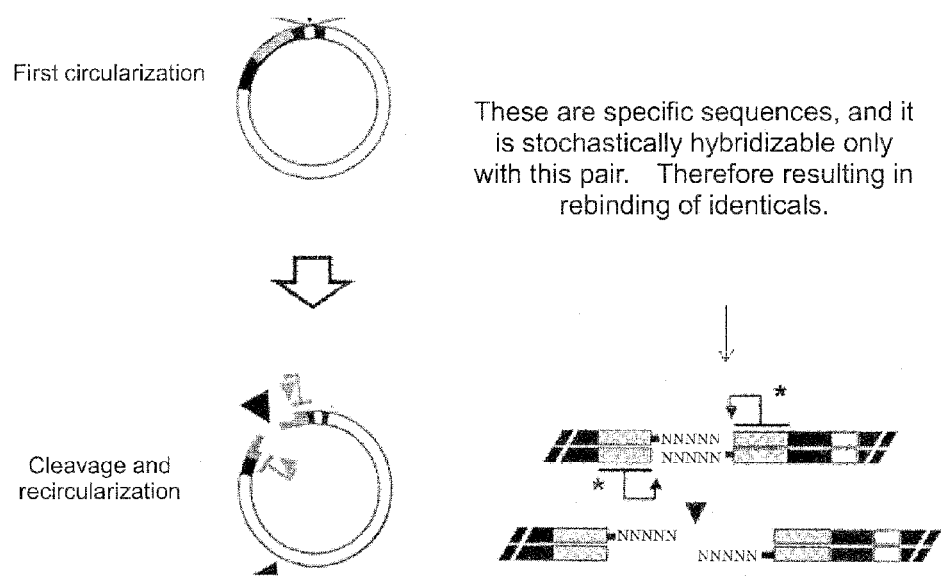
FIG. 6 schematically shows first circularization, second cleavage, and second circularization steps in the two-step circularization method according to the present invention.

Step 3) is a first circularization step of ligating both ends of the DNA molecule obtained in step 2) to circularize the DNA molecule (FIG. 6; first circularization).

Step 4) is a step of eliminating an uncircularized linear single-molecule and a multiple-molecule-bound DNA in step 3).

Step 5) is a second cleavage step of cleaving the circular DNA molecule obtained in step 3) and step 4) with a nick-generating enzyme or a restriction enzyme recognizing the nick-generating enzyme recognition sites or restriction enzyme sites of the adapter (b).

Step 6) is a second circularization step of ligating both ends of the DNA molecule obtained in step 5) to circularize the DNA molecule (FIG. 6; cleavage and recirculization). In this step, because of the specificity of the sequence of the cleavage site, only the cleavage sites from the adapter (b) bound to the same DNA can bind to each other.

In the second embodiment of the present invention, preferably, the adapter (A) is a double-stranded DNA comprising a restriction enzyme site X recognizing a palindromic sequence, and the adapter (B) is a double-stranded DNA consisting of two DNA strands complementary to each other having the following structure $y_1$-Y-$y_2$-X:

[Formula 9]

$$\underbrace{\boxed{\phantom{xx}}\,N_1\text{-}N_2\text{------}N_k\text{------}N_{(n-1)}\text{-}N_n\boxed{\phantom{xx}}}_{y_1}\underbrace{\phantom{xxxx}}_{Y}\underbrace{\boxed{\phantom{xx}}}_{y_2}\underbrace{\boxed{\phantom{xx}}}_{X}$$

$$\underbrace{\boxed{\phantom{xx}}\,N'_1\text{-}N'_2\text{----}N'_k\text{---}N'_{(n-1)}\text{-}N'_n\boxed{\phantom{xx}}}$$

wherein

X represents a double-stranded DNA being a restriction enzyme site recognizing a palindromic sequence;

$y_1$ and $y_2$ represents double-stranded DNAs respectively comprising identical nick-generating enzyme recognition sites or restriction enzyme sites being reversely oriented to each other;

Y represents a double-stranded DNA sequence having a unique sequence for each DNA molecule to be circularized, n represents an integer of 1 to 40, $N_1$ to $N_n$, which may be the same or different, each represent a deoxyribonucleotide selected from the group consisting of dAMP, dCMP, dGMP and dTMP, and $N'_1$ to $N'_n$ represent the following deoxyribonucleotides respectively corresponding to the $N_1$ to $N_n$,

TABLE 3

| $N_k$ | $N'_k$ |
|---|---|
| dAMP | dTMP |
| dCMP | dGMP |
| dGMP | dCMP |
| dTMP | dAMP | wherein k represents an integer from 1 to n.

In the above structure, n is 1 to 40, preferably 4 to 15, and more preferably 5 to 10. However, even if n is more than 40, the method of the present invention can be carried out.

The Y site consists of a pair of nucleotide sequences, which are randomly combined. For example, if Y is constituted with 8 nucleotide sequences, $4^8$ combinations are obtained. Thereby, pair formation in circularization can be specified (selected), and rebinding only to the original pair becomes possible. As a result, only a single DNA can be recircularized, and since the Y portion of another molecule has a different structure, it cannot rebind n thereto.

Since 4 types of nucleic acids are combined in a repeated permutation manner, if an N number of nucleic acids are present in the Y portion, the number of the sequences can be $4^N$. Accordingly, if N is 5, $4^5=1,016$ types of nucleic acids are present in the Y portion. If N is 7, 16,000 or more nucleic acids are present in the Y portion. Thus, N=7 is substantially sufficient. However, there is no problem, even if the number of nucleic acids is 8 or greater. When N is a great number, even if the nucleic acids are partially different, hybridization and ligation can be carried out. When the nucleic acids contain such mismatch, they can be digested using endonuclease. As a method for producing the Y portion of the adapter (B), the Y portion can be basically produced by determining N (the number of nucleic acids), and then carrying out the synthesis of a main chain by random sequential condensation, in which nucleic acids are not determined, and a polymerase extension reaction using primers on consensus sequences.

In the second embodiment of the present invention, preferably, $y_1$ and $y_2$ respectively comprise nick-generating enzyme recognition sites, and more preferably, the nick-generating enzyme is Nb.BtsI. Further, $y_1$ and $y_2$ may preferably comprise restriction enzyme sites.

Regarding a Third Embodiment of the Present Invention

The third embodiment of the present invention provides a preferred adapter (B) used in the method of the above described second embodiment of the present invention, namely, an adapter for producing a circular DNA, consisting of two DNA strands complementary to each other having the following structure $y_1$-Y-$y_2$-X:

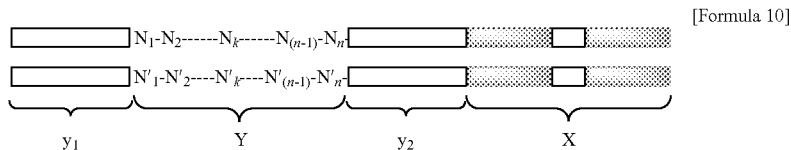

[Formula 10]

wherein
X represents a double-stranded DNA being a site for a restriction enzyme recognizing a palindromic sequence;
$y_1$ and $y_2$ represent double-stranded DNAs respectively comprising identical nick-generating enzyme recognition sites or restriction enzyme sites being reversely oriented to each other;
Y represents a double-stranded DNA sequence having a unique sequence for each DNA molecule to be circularized, n represents an integer of 1 to 40, $N_1$ to $N_n$, which may be the same or different, each represent a deoxyribonucleotide selected from the group consisting of dAMP, dCMP, dGMP and dTMP, and $N'_1$ to $N'_n$ represent the following deoxyribonucleotides respectively corresponding to the $N_1$ to $N_n$,

TABLE 4

| $N_k$ | $N'_k$ |
|---|---|
| dAMP | dTMP |
| dCMP | dGMP |
| dGMP | dCMP |
| dTMP | dAMP | wherein k represents an integer from 1 to n.

In the above structure, n is 1 to 40, preferably 4 to 15, and more preferably 5 to 10. However, even if n is more than 40, the present invention can be carried out.

As with the above described second embodiment, in the third embodiment of the present invention, preferably, $y_1$ and $y_2$ respectively comprise nick-generating enzyme recognition sites, and more preferably, the nick-generating enzyme is Nb.BtsI or Nt.BsqQI. Further, $y_1$ and $y_2$ may preferably comprise restriction enzyme sites.

Regarding a Fourth Embodiment of the Present Invention

The fourth embodiment of the present invention provides a kit for producing a circular DNA, comprising the preferred adapter (A) and adapter (B) used in the method of the above described second embodiment of the present invention. That is to say, the fourth embodiment of the present invention provides a kit for producing a circular DNA, comprising an adapter (A) consisting of double-stranded DNA comprising a restriction enzyme site identical to the restriction enzyme site represented by X according to the above described third embodiment, and an adapter (B) according to the above described third embodiment.

The kit for producing a circular DNA of the present invention comprises an adapter (A) and an adapter (B). These adapters are allowed to bind to both ends of a DNA molecule of interest, and thereafter, the two-step circularization method according to the first or second embodiment of the present invention is carried out, so as to provide a circularized DNA that comprises a circularized DNA formed only from a single-molecule DNA without comprising a circularized DNA formed from a multiple-molecule DNA.

Regarding a Fifth Embodiment of the Present Invention

The fifth embodiment of the present invention provides a method for producing a cDNA library, comprising using the two-step circularization method according to the first or second embodiment of the present invention. By applying the method according to the first or second embodiment of the present invention to a library consisting of linear cDNAs, a cDNA library comprising a circularized DNA consisting only of a single-molecule DNA can be produced.

Regarding a Sixth Embodiment of the Present Invention

The sixth embodiment of the present invention provides a method for identifying a gene by subjecting a circular DNA molecule obtained by using the method according to the first or second embodiment of the present invention to a mate-pair method, the method comprising the following steps:
1) a step of reading nucleotide sequences, each consisting of 1.5 to 600 nucleotides, flanking to both sides of an adapter (B) in a circular DNA molecule obtained by using the method according to the first or second embodiment of the present invention; and
2) a step of identifying a gene contained in the circular DNA molecule by comparing the read nucleotide sequences with the sequences of both ends of a known gene.

Step 1) in the method of the sixth embodiment of the present invention is a step of reading nucleotide sequences, each consisting of 15 to 600 nucleotides, flanking to both sides of the adapter (B) in the circular DNA molecule obtained using the method according to the first or second embodiment of the present invention. The nucleotide sequence to be read consists of preferably 15 to 100 nucleotides, and more preferably 25 to 35 nucleotides. However, the method of the present invention can also be carried out by reading a nucleotide sequence consisting of 600 or more nucleotides. The nucleotide sequence can be read by a method well known to a person skilled in the art, using a sequencer.

Step 2) in the method of the sixth embodiment of the present invention is a step of identifying a gene contained in the circular DNA molecule by comparing the read nucleotide sequences with the sequences of both ends of a known gene. If the read nucleotide sequences, which correspond to the sequences on both ends of a DNA molecule of interest, can be confirmed to be identical to the sequences of both ends of a known gene, then the DNA molecule of interest is identified to be the known gene.

Regarding a Seventh Embodiment of the Present Invention

The seventh embodiment of the present invention provides a method for detecting a fusion gene by subjecting a circular DNA molecule obtained by using the method according to the first or second embodiment of the present invention to a mate-pair method, the method comprising the following steps:
1) a step of reading nucleotide sequences, each consisting of 15 to 600 nucleotides, flanking to both sides of an adapter (B) in a circular DNA molecule obtained by using the method according to the first or second embodiment of the present invention; and
2) a step of comparing the read nucleotide sequences with the sequences of both ends of a known gene, wherein if the genes of both ends correspond to known different genes, the gene comprised in the circular DNA molecule is identified to be a fusion gene.

Step 1) in the method of the seventh embodiment of the present invention is a step of reading nucleotide sequences, each consisting of 15 to 600 nucleotides, flanking to both sides of an adapter (B) in a circular DNA molecule obtained by using the method according to the first or second embodiment of the present invention. The nucleotide sequence to be read consists of preferably to 100 nucleotides, and more preferably 25 to 35 nucleotides. However, the method of the present invention can also be carried out by reading a nucleotide sequence consisting of 600 or more nucleotides. The nucleotide sequence can be read by a method well known to a person skilled in the art, using a sequencer.

Step 2) in the method of the seventh embodiment of the present invention is a step of comparing the read nucleotide sequences with the sequences of both ends of a known gene. Herein, if the genes of both ends correspond to known different genes, the gene comprised in the circular DNA molecule is identified to be a fusion gene. That is to say, if a portion, which corresponds to one end of the read nucleotide sequences corresponding to the sequences on both ends of a DNA molecule of interest, is identical to one end of a known gene, and if a portion corresponding to the other end is identical to one end of another known gene, the DNA molecule of interest is identified to be a fusion gene consisting of two known genes.

As an example, when the sequences of both sides flanking to both sides of the adapter (B) correspond to both ends of a known fusion gene, the DNA of interest is detected to be the known fusion gene. When the relationship between the expression of the known fusion gene and a disease has been known, it is possible to detect a disease characterized by the expression of the fusion gene detected by the aforementioned method, using the fusion gene as a marker.

As another example, when the sequences flanking to both sides of the adapter (B) correspond to the terminal sequences of different genes and do not correspond to both ends of a known fusion gene, the gene contained in the circular DNA molecule is identified to be a novel fusion gene. The novel fusion gene detected by the aforementioned method can be used in drug discovery screening.

EXAMPLES

Specific methods of allowing adapters to bind to both ends of a DNA molecule of interest (the left and right ends of a DNA molecule of interest) will be described in the following examples.

Example 1

Figure 7:
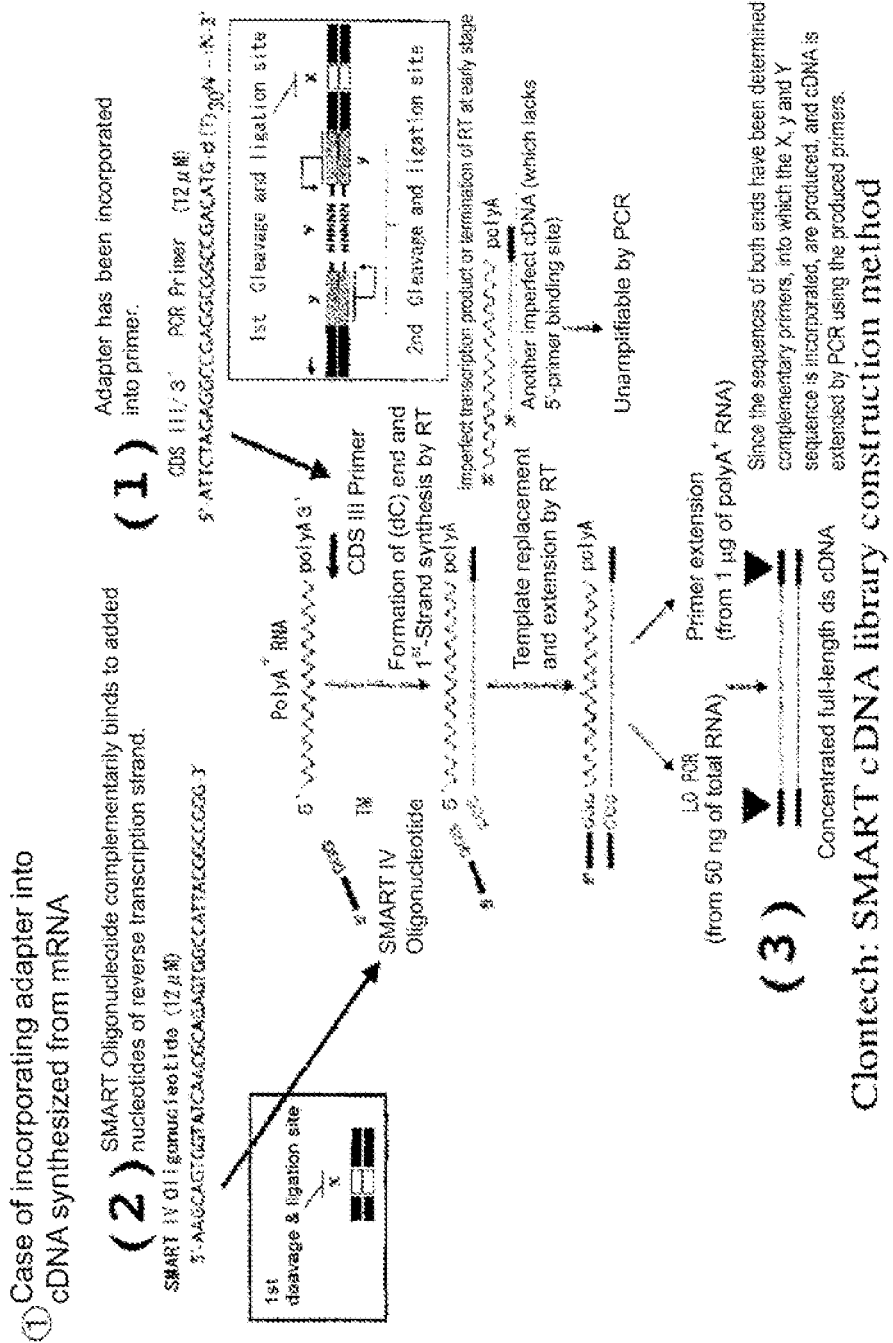
FIG. 7 is a schematic view showing application of the method of the present invention to cDNA synthesized from mRNA.
Figure 3:
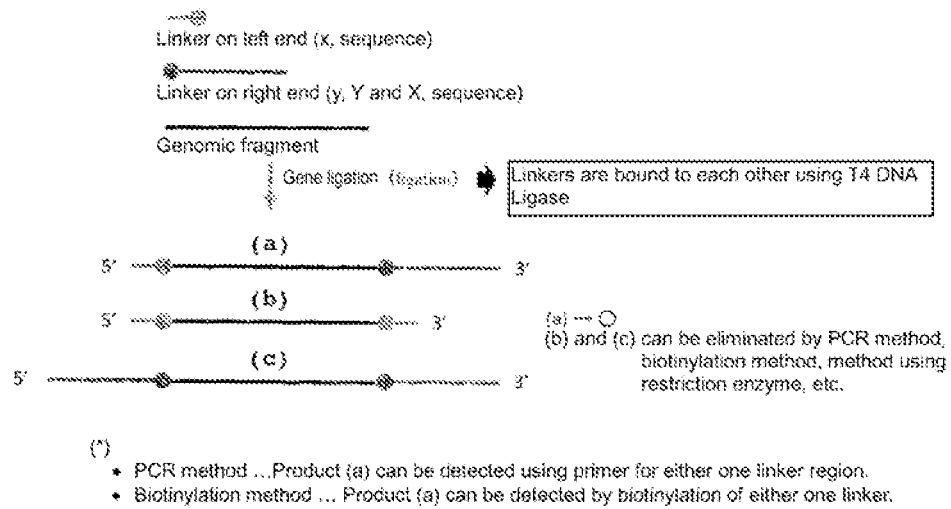
Figure 9:
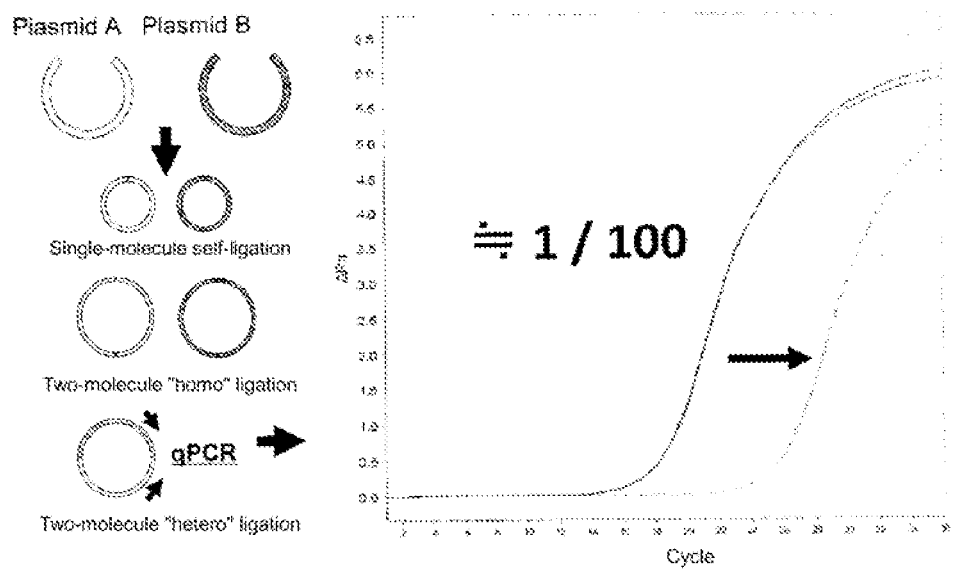
FIG. 9 shows the experimental results of Example 4, which demonstrate that the production amount of a circularized DNA consisting of a plurality of molecules is decreased by application of the method of the present invention.

Application of the Method of the Present Invention to the Discovery of a Fusion Gene, in which cDNA Synthesized from mRNA is Used When a cDNA library is synthesized from mRNA, in the most common method (Clontech SMART cDNA method) among the currently used methods, complementary strand DNA is first synthesized with reverse transcriptase, using oligonucleotide (1) having a poly T sequence complementary to a poly A site at the 3'-terminus of mRNA, as shown in FIG. 7. After completion of the synthesis, a specific oligonucleotide sequence (2) is incorporated at the 5'-terminus of mRNA, as shown in FIG. 7. Subsequently, DNA is synthesized from an oligonucleotide complementary to this specific sequence, or a cDNA library is produced by PCR.

In Case the Adapters of the Present Invention are Incorporated into cDNA at the Same Time with the cDNA Synthesis In this case, the adapter (B) has been introduced into the oligonucleotide (1) sequence having a poly T sequence complementary to a poly A site at the 3'-terminus of mRNA, and the adapter (A) has been added to the oligonucleotide (2) sequence. Thus, when a cDNA library is synthesized, it automatically becomes the basic structure of the present invention. It is not necessary to bind new sequences to the right and left ends, and the routine can directly proceed to the next step. By this method, when the cDNA library is further amplified by PCR, if it is directly amplified, a specific N nucleotide sequence must be amplified. Hence, since the diversity of the N nucleotide is maintained, amplification is carried out using, for example, a 5' phosphate group-added primer as an upstream primer, and a primer containing the N nucleotide as a downstream primer, and after completion of the PCR, a strand into which the phosphate group primer has been incorporated is digested with λ exonuclease. Thereafter, primer-extension is carried out again from the upstream primer, so as to produce a cDNA library in which the diversity of the N nucleotide is maintained. However, in the case of the adapter binding method, this process is not necessary. In order to introduce the adapter of the present invention after modification, such as fragmentation of the library, the subsequent adapter binding method is carried out.

In Case the Adapter of the Present Invention is Incorporated into cDNA after Ordinary cDNA Synthesis When a cDNA library is produced, it is possible that a restriction enzyme sequence has been introduced into each of the 3'-terminus and 5'-terminus thereof, as shown in FIG. 7(3). As a restriction enzyme used in this case, either an ordinary palindromic sequence, or a non-palindromic sequence for distinguishing the 3'-terminus and 5'-terminus, can be used. Moreover, in order to ensure adapter binding, the adapter can also be bound to an end in the shape of blunt end with an A-protruding nucleotide. In order to introduce the adapter of the present invention after modification of the library, this method is desirable.

Example 2

Application of the Method of the Present Invention to Genomic Analysis by Mate-Pair Method When genome is targeted, the situation is different from the case of a cDNA library. Differing from cDNA, a genomic fragment cannot distinguish the left and right sides of a DNA fragment. Accordingly, as shown in FIG. 8, only the product (a) in FIG. 8, namely, a product prepared by binding the adapter on the left end to the adapter on the right end so that the two adapters are appropriately ligated, can be selected by a PCR method or a biotinylation method, or by inserting non-palindromic sequences as a restriction enzyme X sequence into both ends, or a method of establishing a plurality of restriction enzyme sites at the same site, using restriction enzyme (BstXI, etc.) containing an N region, etc.

Regarding Adapters (A) and (B) Added to Both Ends of a DNA Molecule

Basically, the following method is adopted to add adapters (A) and (B) to both ends of a DNA molecule. At first, to a group of a plurality of DNAs, the concentration of which has been almost determined depending on the number of DNA molecules of interest, an adapter (A) is first allowed to bind. In this case, the amount of the adapter (A) added is set to be smaller than the amount of the target DNA molecules. However, stoichiometrically, the number of the adapters (A) may be the same as the number of the target DNA molecules, or one nucleotide protrusion may be enzymatically produced on a DNA fragment and a complementary adapter may be allowed to bind thereto. Especially, in this case, the concentration of the adapter may be excessive. Thereby, the adapter (A) is allowed to bind to the end of the DNA molecule. Subsequently, an adapter (B) is allowed to bind.

In the present invention, as shown in (a) of FIG. 8, it is necessary to produce a molecule in which the adapter (A) binds to one end thereof and the adapter (B) binds to the other end. Herein, as shown in (b) or (c) of FIG. 8, it is necessary to eliminate a DNA molecule to which only the adapter (A) binds ((b) of FIG. 8) and a DNA molecule to which only the adapter (C) binds ((c) of FIG. 8). The methods therefor will be described below.

In Case of Using a Non-Palindromic Sequence to a First Restriction Enzyme X Site In the case of a molecule of type (a) of FIG. 8, a first circularization, nick cleavage, and a second circularization are carried out without problems, and as a result, circularized DNA of interest is produced without problems.

On the other hand, in the case of a molecule of type (b) of FIG. 8, the first circularization is impossible for a single molecule and thus, it is eliminated. However, circularization with a plurality of DNAs can be formed (for example, the binding of two molecules, namely, the binding of the molecule of type (b) to the molecule of type (c)). Such a plurality of DNA molecules must bind to the molecule of type (a) or type (c) as a binding partner. Accordingly, both sides must bind to specific sequences having N sequences. Thus, after completion of the nick cleavage, the second circularization cannot be formed and is eliminated.

Moreover, in the case of a molecule of type (c) of FIG. 8, the first circularization is impossible for a single molecule and is eliminated. However, circularization with a plurality of DNAs can be formed (for example, the binding of two molecules, namely, the binding of the molecule of type (b) to the molecule of type (c)). Since this DNA fragment originally has different N sequences on both ends, after completion of the nick cleavage, the second circularization cannot be formed and is eliminated.

In Case of Using a Palindromic Sequence to a First Restriction Enzyme X Site

In the case of a molecule of type (a) of FIG. 8, a first circularization, nick cleavage, and a second circularization are carried out without problems, and as a result, circularized DNA of interest is produced without problems.

On the other hand, in the case of a molecule of type (b) of FIG. 8, the first circularization is possible. However, since this molecule does not have a nick sequence, nick cleavage is not carried out, and it remains as circularized DNA and cannot be eliminated. As an example of a method of preventing this, there is a BstXI method as described below.

Moreover, in the case of a molecule of type (c) of FIG. 8, the first circularization and nick cleavage are possible. However, since this molecule originally has different N sequences on both ends, after completion of the nick cleavage, the second circularization cannot be formed and is eliminated.

Regarding BstXI Method

In a case in which adapters (A) are added to both ends, both ends are ligated at a first stage. However, since cleavage does not take place at a second stage, it remains as circular DNA. As a method of solving this problem, BstXI is added to the outside of the adapter (A) comprising the restriction enzyme site, for example. Specifically, into the following restriction enzyme BstXI site, an EcoRI site is incorporated, so that CCANNNNNTGG is converted to CCAGAATTCTGG, for example.

[Formula 11]

```
BstXI (restriction enzyme)
    ∇
CCANNNNNTGG
GGTNNNNNACC
    Δ
In this case, the number N is limited to 4
nucleotides.
```

That is to say, in this method, the restriction enzyme site of each of the adapter (A), and the adapter (A) contained in the adapter (B), is set to be an EcoRI site, for example. Then, only in the case of the adapter (A), the sequence outside the EcoRI site is set to be a BstXI recognition sequence, for example. That is, the sequence of the adapter (A) is set to be CCA-GAATTCTGG. On the other hand, the adapter (A) contained in the adapter (B) comprises an EcoRI site but does not comprise a BstXI recognition sequence, so that it cannot be cleaved with BstXI.

As a result, if the two adapters (A) bind to both ends and are then associated with each other, circularization can be opened by cleaving with BstXI and can be then eliminated. Of course, if the adapter (A) binds to the adapter (B), since the adapter (B) does not have a BstXI recognition sequence, it cannot be cleaved with BstXI.

According to the above described method, the method of the present invention can be applied even to a genomic DNA fragment that cannot distinguish between upstream and downstream, differing from cDNA, so that single-molecule circular DNA can be produced, and so that the accuracy of mate-pair analysis can be significantly improved.

Example 3

Regarding the Possibility of Rebinding of Circular DNA Genes in a Plurality of Circular DNA Molecules Such possibility can be fully ignored, stochastically. The grounds will be described below.

In order to stochastically assume the possibility that separated genes are re-associated, such possibility is estimated in the following three cases: (1) a case in which the possibility is assumed from the volume of a DNA molecule and the amount (volume) of a reaction solution; (2) a case in which the possibility is assumed from the number of molecules in the reaction solution (in the two above cases, it is assumed that the number of N nucleotides in the Y portion is sufficiently large and that it has high specificity); and further, (3) a case in which the number of N nucleotides is determined but it is not sufficiently large.

(1) The Case in which the Possibility is Assumed from the Volume of a DNA Molecule and the Amount (Volume) of a Reaction Solution First, a single DNA molecule is presumed to be a sphere and its volume is estimated. Then, the possibility that molecules that have once been separated in a reaction system are associated as spheres in a solution is estimated.

The length of one nucleotide: 0.34 nm (0.34×10e-9 m=3.4×10e-8 mm), the length of a 3-kbp (3000 bp) plasmid: 1×10e-4 mm, the volume of a DNA molecule assumed to be a sphere: 4/3×3.14×(1×10e-4)×(1×10e-4)×(1×10e-4) mm3=4×10e-12 mm3, and the number of DNA molecules as spheres in 100 ul if the volume of a single molecule is presumed to be 4×100e-12 mm3: 100 mm3/4×10e-12 mm3=2.5×10e13.

Accordingly, if the reaction system is homogeneous, the possibility that a sphere is associated with another equivalent sphere complementary thereto is extremely small ((1/(2.5× 10e13))=4×100e-14).

(2) The Case in which the Possibility is Assumed from the Number of Molecules in the Reaction Solution On the other hand, the number of molecules is calculated as follows.

The molecular weight of a 3-kbp plasmid: 625×3000=1.8× 10e6, the mass of 1 mole of plasmid: 1 mol/L=1.8×10e6 g/1 L=1.8×10e12 ug/1 L, the molar number of 3 ug of plasmid: 1 (mol/L)×3 ug/(1.8× 10e12) ug=3/1.8×10e-12 mol/L=1.6×10e-12 mol/L=1.6× 10e-9 mol/ml, and the number of molecules of 3 ug of plasmid dissolved in 1 ml of solution if the Avogadro's number is presumed to be 6×10e23: 1.6×10e-9 mol/ml×6×10e23=1.6×6×10e14=1× 10e15.

Accordingly, if 3 ug of plasmid is present in 100 ul of reaction system, since 100 ul=10e-1 mm3, the number of molecules is 1×10e14.

The possibility that a molecule in the solution with the aforementioned number of molecules is associated with another equivalent molecule complementary thereto is extremely small (1/1×10e14).

(3) As Described Above, it is Assumed that the Specificity of the Number of N Nucleotides in the Y Portion would Rather Contribute to Rebinding of Separated Genes.

When the number of N nucleotides is "5," the possibility that two identical genes separated are rebound via identical gene fragments is: ((¼)×(¼)×(¼)×(¼)× (¼))×((¼)×(¼)×(¼)×(¼)×(¼))=1×10e-6.

Accordingly, from these estimations, it can be concluded that the possibility that, after a plurality of DNAs have formed a ring and they have been then separated, identical DNA molecules rebind to each other, is extremely low, and thus, it can be fully ignored.

Example 4

Production of Circularized DNA from Single-Molecule DNA

The following experiment was carried out to verify that noise in circularization with a plurality of DNA molecules is reduced by increasing the efficiency of circularization with single-molecule DNA according to a two-step DNA binding (ligation) method.

Two types of plasmids, Plasmid A and Plasmid B, were prepared. Product (i) obtained by cleaving each plasmid with a restriction enzyme and then directly ligating the fragments was compared with product (ii) obtained by ligating the adapter of the present invention according to the two-step ligation.

In the case of the product (ii) to which the method of the present invention was applied, any given nucleotides N (6 nucleotides) used as an adapter were subjected to random synthesis, and after ligation of the adapter, the adapter was cleaved at an NcoI site present on the end of the adapter. Then, a mixture of these plasmids was circularized by a first-step ligation, and using Nick enzyme, Nick was placed before and after any given 6 nucleotides N, so that circularization was cleaved. Thereafter, ligation was carried out again to perform a second-step circularization.

It is predicted that, during this operation, the products (i) and (ii) in the mixed solution would comprise (1) circularized DNA formed with a single molecule of Plasmid A, (2) circularized DNA formed with a single molecule of Plasmid B, (3) circularized DNA formed with a plurality of molecules of Plasmid A, (4) circularized DNA formed with a plurality of molecules of Plasmid B, and (5) circularized DNA formed with a plurality of molecules comprising Plasmid A and Plasmid B.

According to the present invention, it was anticipated that the above-mentioned circularized DNAs (3), (4), and (5) would be significantly decreased in the product (ii), in comparison with the product (i).

Hence, the amount of the circularized DNA (5) in the mixed solution generated from these products (i) and (ii) was evaluated as a representative example. Quantitative PCR was carried out using PCR primers specific to Plasmid A and Plasmid B.

As a result, it was confirmed that the amount of the circularized DNA formed with a plurality of molecules such as (5) above, which was considered as noise, could be reduced to approximately one-hundredth by applying the method of the present invention (ii), in comparison with the method (i).

INDUSTRIAL APPLICABILITY

Using the adapter and method of the present invention, the accuracy of gene analysis is significantly improved. In addition, unconventional high-accuracy mate-pair analysis becomes possible, and thus, the adapter and method of the present invention are provided as tools extremely useful for genomic analysis. In particular, by applying the method of the present invention to the production of a cDNA library, it is highly likely to discover a novel fusion gene. That is to say, by reliably achieving circularization of a single DNA molecule, it becomes possible to develop novel diagnostic tool and/or method.

According to the present invention, a method for circularizing only a single-molecule DNA, wherein circularization of a plurality of molecules is substantially prevented with regard to circularization of DNA, is provided, so that problems regarding contamination in gene analysis such as mate-pair analysis can be solved, and so that high-accuracy analysis becomes possible. Moreover, by applying the method of the present invention to detection and/or analysis of a fusion gene, high-accuracy analysis of a fusion gene becomes possible, and a useful diagnostic tool can be provided.

The invention claimed is:

1. A method for producing a circular DNA, the method comprising the following steps:
   1) providing a DNA molecule;
   2) a step of covalently binding an adapter (A) to one end of the DNA molecule, and covalently binding to the other end of the DNA molecule an adapter (B) comprising an adapter (b) and the adapter (A), wherein:
      the adapter (B) binds to the DNA molecule via the adapter (b) and not the adapter (A),
      the adapter (A) comprises a cleavage site capable of generating a cleavage end which can non-specifically bind to any cleavage end of the adapter (A), and
      the adapter (b) comprises a cleavage site capable of generating a cleavage end which can specifically bind only to the cleavage end from the same adapter (b);
   3) a first cleavage step of cleaving the DNA molecule obtained in step 2) at the cleavage site of each of the adapters (A);
   4) a first circularization step of binding both ends of the DNA molecule obtained in step 3) to circularize the DNA molecule;
   5) a step of eliminating uncircularized linear DNA molecules obtained in step 4);
   6) a second cleavage step of cleaving the circular DNA molecules from step 5) at the cleavage site of the adapter (b); and
   7) a second circularization step of binding both ends of the DNA molecule obtained in step 6) to circularize the DNA molecule and obtain a circular DNA.

2. A method for producing a circular DNA, the method comprising the following steps:
   1) providing a DNA molecule;
   1) providing a DNA molecule consisting of the single gene;
   2) a step of covalently binding an adapter (A) to one end of the DNA molecule, and covalently binding to the other end of the DNA molecule an adapter (B) comprising an adapter (b) and the adapter (A), wherein:
      the adapter (B) binds to the DNA molecule via the adapter (b) and not the adapter (A),
      the adapter (A) is a double-stranded DNA comprising a restriction enzyme recognition site comprising a palindromic sequence, and
      the adapter (B) comprises the adapter (b) and the adapter (A), wherein:
      the adapter (b) is a double-stranded DNA comprising identical nick-generating enzyme recognition sites being reversely oriented to each other, wherein the adapter (b) is a double-stranded DNA comprising a double-stranded DNA sequence having a unique sequence for each adapter (b) between the identical nick-generating enzyme recognition sites being reversely oriented to each other, said unique sequence consisting of 4 to 15 nucleotides, and if the adapter (b) is cleaved at the identical nick-generating enzyme recognition sites being reversely oriented to each other, the cleavage site rebinds only to the cleavage site from the same adapter (b);
   3) a first cleavage step of cleaving the DNA molecule obtained in step 2) with the restriction enzyme which recognizes the restriction enzyme recognition site comprised in the adapter (A);
   4) a first circularization step of ligating both ends of the DNA molecule obtained in step 3) to circularize the DNA molecule;
   5) a step of eliminating uncircularized linear DNA molecules obtained in step 4);
   6) a second cleavage step of cleaving the circular DNA molecules from step 5) with a nick-generating enzyme recognizing the nick-generating enzyme recognition sites or restriction enzyme sites of the adapter (b); and
   7) a second circularization step of binding both ends of the DNA molecule obtained in step 6) to circularize the DNA molecule and obtain a circular DNA.

3. The method according to claim 2, which further comprises a step of digesting with endonuclease a circularized DNA formed by binding the adapters (b) via cleavage sequence sites being partially different from each other and circularization in step 7) of claim 2.

4. The method according to claim 2, wherein
   the adapter (A) is a double-stranded DNA comprising a restriction enzyme recognition site X comprising a palindromic sequence, and
   the adapter (B) is a double-stranded DNA consisting of two DNA strands complementary to each other having the following structure $y_1$-Y-$y_2$-X:

[Formula 1]

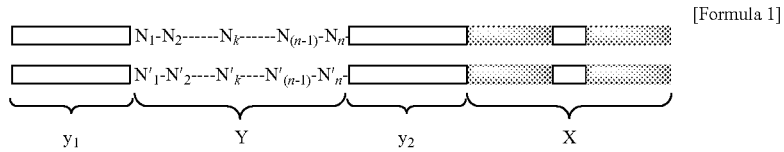

wherein

X represents a double-stranded DNA being a restriction enzyme recognition site comprising a palindromic sequence; $y_1$ and $y_2$ represent double-stranded DNAs respectively comprising identical nick-generating enzyme recognition sites being reversely oriented to each other;

Y represents a double-stranded DNA sequence having a unique sequence for each DNA molecule to be circularized, n represents an integer from 4 to 15, $N_1$ to $N_n$, which may be the same or different, each represent a deoxyribonucleotide selected from the group consisting of dAMP, dCMP, dGMP and dTMP, and $N'_1$ to $N'_n$ represent the following deoxyribonucleotides respectively corresponding to the $N_1$ to $N_n$,

TABLE 1

| $N_k$ | $N'_k$ |
|-------|--------|
| dAMP  | dTMP   |
| dCMP  | dGMP   |
| dGMP  | dCMP   |
| dTMP  | dAMP   | wherein k represents an integer from 1 to n.

5. The method according to claim 4, wherein the nick-generating enzyme is Nb.BtsI or Nt.BsqQI.

6. A method for producing a cDNA library, comprising performing the method according to claim 1 to produce the cDNA library.

7. A method for identifying a gene by subjecting a circular DNA molecule obtained by using the method according to claim 1 to a mate-pair method, the method comprising the following steps:
1) a step of reading nucleotide sequences, each consisting of 15 to 600 nucleotides, flanking to both sides of an adapter (B) in a circular DNA molecule obtained by using the method according to claim 1; and
2) a step of identifying a gene contained in the circular DNA molecule by comparing the read nucleotide sequences with the sequences of both ends of a known gene.

8. A method for detecting a fusion gene by subjecting a circular DNA molecule obtained by using the method according to claim 1 to a mate-pair method, the method comprising the following steps:
1) a step of reading nucleotide sequences each consisting of 15 nucleotides or more and 600 nucleotides or less that are flanking to both sides of an adapter (B) in a circular DNA molecule obtained by using the method according to claim 1; and
2) a step of comparing the read nucleotide sequences with the sequences of both ends of a known gene, wherein if the genes of both ends correspond to known different genes, the gene comprised in the circular DNA molecule is identified to be a fusion gene.

9. The method for detecting a fusion gene according to claim 8, wherein the sequences of both sides flanking to both sides of the adapter (B) correspond to both ends of a known fusion gene.

10. A method for detecting a disease characterized by the expression of the fusion gene detected by the method according to claim 8, wherein the fusion gene is used as a marker.

11. The method according to claim 8, wherein if the sequences flanking to both sides of the adapter (B) correspond to the terminal sequences of different genes and do not correspond to both ends of a known fusion gene, the gene comprised in the circular DNA molecule is identified to be a novel fusion gene.

\* \* \* \* \*